(12) United States Patent
Yang et al.

(10) Patent No.: US 8,906,981 B2
(45) Date of Patent: Dec. 9, 2014

(54) DENTAL COMPOSITIONS COMPRISING SEMI-CRYSTALLINE RESIN AND NANOCLUSTER FILLER

(75) Inventors: Jie Yang, Woodbury, MN (US); Naimul Karim, Maplewood, MN (US); Todd D. Jones, St. Paul, MN (US); Dwight W. Jacobs, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/814,974

(22) PCT Filed: Aug. 31, 2011

(86) PCT No.: PCT/US2011/049832
§ 371 (c)(1),
(2), (4) Date: Feb. 8, 2013

(87) PCT Pub. No.: WO2012/057917
PCT Pub. Date: May 3, 2012

(65) Prior Publication Data
US 2013/0210959 A1  Aug. 15, 2013

Related U.S. Application Data

(60) Provisional application No. 61/407,222, filed on Oct. 27, 2010.

(51) Int. Cl.
| | | |
|---|---|---|
| A61K 6/083 | (2006.01) | |
| A61C 13/00 | (2006.01) | |
| A61C 5/08 | (2006.01) | |
| C08L 33/10 | (2006.01) | |
| C08L 67/07 | (2006.01) | |
| A61K 6/087 | (2006.01) | |
| A61K 6/00 | (2006.01) | |

(52) U.S. Cl.
CPC .............. *A61K 6/087* (2013.01); *A61K 6/0002* (2013.01); *A61K 6/0073* (2013.01); *A61K 6/083* (2013.01); *A61C 5/08* (2013.01); *A61C 13/00* (2013.01)
USPC ..................................................... 523/115

(58) Field of Classification Search
None
See application file for complete search history.

(56) References Cited

U.S. PATENT DOCUMENTS

| | | | |
|---|---|---|---|
| 4,503,169 A | 3/1985 | Randklev | |
| 4,642,126 A | 2/1987 | Zador | |
| 4,652,274 A | 3/1987 | Boettcher | |
| 4,695,251 A | 9/1987 | Randklev | |
| 5,403,188 A | 4/1995 | Oxman | |
| 5,545,676 A | 8/1996 | Palazzotto | |
| 6,030,606 A * | 2/2000 | Holmes ........................... | 424/49 |
| 6,355,545 B1 | 3/2002 | Ohba | |
| 6,506,816 B1 * | 1/2003 | Ario et al. ..................... | 523/116 |
| 6,572,693 B1 | 6/2003 | Wu | |
| 6,624,211 B2 | 9/2003 | Karim | |
| 6,730,156 B1 * | 5/2004 | Windisch et al. ............... | 106/35 |
| 7,674,850 B2 | 3/2010 | Karim | |
| 7,816,423 B2 | 10/2010 | Karim | |
| 2003/0114553 A1 | 6/2003 | Karim | |
| 2005/0100868 A1 | 5/2005 | Karim | |
| 2009/0118389 A1 | 5/2009 | Abuelyaman | |
| 2009/0305195 A1 * | 12/2009 | Jones et al. ................... | 433/219 |
| 2009/0305196 A1 * | 12/2009 | Karim et al. ............... | 433/222.1 |
| 2012/0202170 A1 | 8/2012 | Johnson | |
| 2012/0251979 A1 | 10/2012 | Karim | |
| 2013/0012614 A1 | 1/2013 | Abuelyaman | |

FOREIGN PATENT DOCUMENTS

| | | |
|---|---|---|
| EP | 2008636 | 12/2008 |
| WO | WO 03/015720 | 2/2003 |
| WO | WO 2006/020760 | 2/2006 |
| WO | WO 2008/008288 | 1/2008 |
| WO | WO 2008/033758 | 3/2008 |
| WO | WO 2010/027676 | 3/2010 |
| WO | WO 2010/048067 | 4/2010 |
| WO | WO 2010/093534 | 8/2010 |

OTHER PUBLICATIONS

Pallav et al., Wear rates of composites, an amalgam, and enamel under stress-bearing conditions:, Journal of Prosthetic Dentistry (Apr. 1998) vol. 59, No. 4, pp. 426-429.
Surface & Colloid Science, vol. 6, ed. Matijevic, E. Wiley Interscience, 1973, pp. 23-29.
Watts et al., "Determination of Polymerization Shrinkage Kinetics in Visible Light-Cured Materials: Methods Development", Dental Materials, Oct. 1991, pp. 281-286.
International Search Report PCT/US2011/049832, Jan. 25, 2012, 5 pgs.
Perstorp Product Data Sheet, Capa® 2200A, 1 page, undated.
Perstorp, Product Data Sheet, Capa® 2200, 1 page, undated.
Perstorp, Product Data Sheet, Capa® 2205, 1 page, undated.
Perstorp, Product Data Sheet, Capa® 2125, 1 page, undated.
Tone Polyols for Coating Applications, Dow Chemical Company brochure, pp. 1-12, May 2002.

* cited by examiner

*Primary Examiner* — James J Seidleck
*Assistant Examiner* — Peter A Salamon
(74) *Attorney, Agent, or Firm* — Carolyn A. Fischer

(57) ABSTRACT

Curable dental compositions, dental articles, and methods of making or using such compositions or articles are described. In one embodiment, the curable dental restoration composition comprises a resin system comprising a free-radically polymerizable semi-crystalline resin having a molecular weight no greater than 3000 g/mole and at least 50 wt-% of nanocluster filler.

45 Claims, No Drawings

DENTAL COMPOSITIONS COMPRISING SEMI-CRYSTALLINE RESIN AND NANOCLUSTER FILLER

BACKGROUND

U.S. Pat. Nos. 7,674,850 and 7,816,423 describe compositions, particularly for forming dental products, having a hardenable self-supporting structure with sufficient malleability to be subsequently customized into a second shape and then hardened, and methods.

US2009/0305196 describes dental compositions that include a polymerizable component and an organogelator. In certain embodiments, the hardenable composition can be in the form of a hardenable, self-supporting (i.e., free-standing) structure having a first shape. The self-supporting structure has sufficient malleability to be reformed into a second shape, thereby providing for simplified customization of a device, e.g., simplified customized fitting of a dental prosthetic device. Once reformed into a second shape, the composition can be hardened using, for example, a free radical curing mechanism under standard photopolymerization conditions to form a hardened composition with improved mechanical properties.

SUMMARY

Although various curable dental restoration compositions and preformed dental articles have been described; industry would find advantage in curable dental compositions, dental articles, and method of making or using such compositions or articles having improved properties.

In one embodiment, a curable dental restoration composition is described comprising a resin system comprising a free-radically polymerizable semi-crystalline resin having a molecular weight no greater than 2000 g/mole and at least 50 wt-% of nanocluster filler.

In another embodiment, a preformed semi-finished dental article is described comprising the described uncured dental restoration composition. The uncured dental restoration composition has a first shape (such as a near net-shaped crown) that is sufficiently malleable to be formed into a second shape.

In yet another embodiment, a method of making a (e.g. finished) dental article comprising providing a semi-finished uncured dental article having a first shape wherein the uncured dental article comprises the described uncured dental restoration composition, forming the semi-finished uncured dental article into a second shape, and hardening by curing.

In each of these embodiments, semi-crystalline resin preferably comprises polycaprolactone units. The resin system typically comprises at least one multi-(meth)acrylate aromatic monomer. Favored multi-(meth)acrylate aromatic monomers include low shrinkage resins derived from bisphenol A. The composition typically comprises one or more additional nanoscopic particulate fillers. Preferred concentrations ranges for the components of the dental restoration composition are described herein.

DETAILED DESCRIPTION OF PREFERRED EMBODIMENTS OF THE INVENTION

The present invention provides a composition that includes a resin system, a filler system, and an initiator system in the form of a hardenable self-supporting (i.e., free-standing) structure having a first shape, preferably the shape of a dental crown. The resin system (one or more resins), filler system (one or more fillers), and initiator system (one or more initiators) are chosen such that: the composition can be relatively easily molded to form the initial self-supporting structure; the self-supporting structure maintains its first shape at room temperature for at least about two weeks (in the absence of conditions that activate the initiator system and in the absence of an external force other than gravity), and the self-supporting structure has sufficient malleability to be reformed into a second shape (preferably at a temperature of about 15° C. to 38° C., more preferably, at a temperature of about 20° C. to 38° C., and most preferably, at room temperature).

Herein, the "resin system" can include one or more resins, each of which can include one or more monomers, oligomers, and/or polymerizable polymers.

The term "self-supporting" means that the composition is dimensionally stable and will maintain its shape (e.g., preformed shape of a crown) without significant deformation at room temperature (i.e., about 20° C. to about 25° C.) for at least about two weeks when free-standing (i.e., without the support of packaging or a container). Preferably, the compositions of the present invention are dimensionally stable at room temperature for at least about one month, and more preferably, for at least about six months. Preferably, the compositions of the present invention are dimensionally stable at temperatures above room temperature, more preferably up to about 40° C., even more preferably up to about 50° C., and even more preferably up to about 60° C. This definition applies in the absence of conditions that activate the initiator system and in the absence of an external force other than gravity.

The term "sufficient malleability" means that the self-supporting structure is capable of being custom shaped and fitted, for example, to a patient's mouth, under a moderate force (i.e., a force that ranges from light finger pressure to that applied with manual operation of a small hand tool, such as a dental composite instrument).

The combination of highly malleable properties (preferably without heating above room temperature or body temperature) before hardening (e.g., cure) and high strength (preferably, a flexural strength of at least about 25 MPa) after hardening provides a composition with numerous potential applications. These applications include, but are not limited to, dental restoratives and dental prostheses, including, but not limited to, temporary, intermediate, and permanent crowns and bridges, inlays, onlays, veneers, articles for implants, dentures, and artificial teeth, orthodontic appliances (e.g., retainers, night guards), tooth facsimiles or splints, maxillofacial prosthesis, and other customized structures. The compositions of the present invention can also be used as filling materials (particularly packable materials), for example.

The compositions of the present invention can be in the form of a variety of dental products, which can be in rope form (as for filling materials), globular form, sheet form, or in the form of a preformed article, which is in a complex or semi-finished shape (as that of a preformed crown). Typically, the dental products referred to herein are in a hardenable form, but the term can also be used for the final dental product in its hardened form.

Preferred dental products include a preformed crown, a preformed inlay, a preformed onlay, a preformed bridge, a preformed veneer, a preformed orthodontic appliance, a preformed maxillofacial prosthesis, a preformed tooth facsimile, or a preformed tooth splint. Alternatively, the dental product can be a filling material (such as a packable material). Particularly preferred dental products include a preformed crown and a preformed bridge, and more preferably, a preformed crown.

Preferred preformed articles for dental implants include healing caps as well as article having tooth-shaped supragingival surfaces as described in WO2010/093534. Further, such articles may comprise an embedded implant abutment, such as described in U.S. Provisional Application Ser. No. 61/255,638, filed Oct. 28, 2009 and U.S. Provisional Application Ser. No. 61/372,706, filed Aug. 11, 2010.

In one preferred embodiment, the present invention provides a preformed dental crown that includes a composition including a resin system, a filler system, and an initiator system, wherein the composition is in the form of a hardenable self-supporting structure having a first shape and sufficient malleability to be formed into a second shape.

The present invention also provides a method of preparing a dental product. The method includes: providing a composition comprising a resin system, a filler system, and an initiator system, wherein the composition is in the form of a hardenable, self-supporting, malleable structure having a first semi-finished shape (e.g., that of a preformed crown or preformed bridge); forming the self-supporting, malleable structure into a second shape; and hardening the self-supporting structure having the second shape to form a dental product. Preferably, forming the self-supporting, malleable structure into a second shape occurs at a temperature of about 15° C. to 38° C. Herein, forming the self-supporting, malleable structure into a second shape occurs under a force that ranges from light finger pressure to that applied with manual operation of a small hand tool, such as a dental composite instrument.

The present invention provides a composition that includes a resin system, a filler system, and an initiator system in the form of a hardenable self-supporting (i.e., free-standing) structure having a first shape, preferably the shape of a dental crown. The resin system (one or more resins), filler system (one or more fillers), and initiator system (one or more initiators) are chosen such that: the composition can be relatively easily molded to form the initial self-supporting structure; the self-supporting structure maintains its first shape at room temperature for at least about two weeks (in the absence of conditions that activate the initiator system and in the absence of an external force other than gravity), and the self-supporting structure has sufficient malleability to be reformed into a second shape (preferably at a temperature of about 15° C. to 38° C., more preferably, at a temperature of about 20° C. to 38° C., and most preferably, at room temperature).

The compositions of the present invention are particularly well suited for preformed dental products. As used herein, a preformed dental product is one that is provided to the dentist in the desired semi-finished shape (a first shape), which can then be modified (e.g., molded, adapted, trimmed) for fit in a patient (a second shape). Herein, a semi-finished shape of a preformed article is the facsimile of what the final shaped article is to be, and is not the shape of a rope, globule, or sheet. This is described in greater detail below. Typically, this means that the compositions of the present invention have been formed into a shape, preferably using a mold with a positive and negative impression, and the resultant shaped material released from the shaping device, preferably a mold, without significant deformation.

Although the compositions of the present invention are particularly useful for preformed crowns and other preformed dental products having a complex shape, they can be used as materials for preparing fillings, etc. The requirements for the latter are less stringent when it comes to molding, removal from a mold, packaging, transportation, and the like, than is required for preformed crowns or other preformed dental articles of a complex shape, typically because filling materials are provided to the dentist in a rope form.

Generally, hardenable self-supporting compositions of the present invention have rheological properties similar to waxes below the waxes' melting points in that they can be relatively easily deformed (i.e., they are malleable) and exhibit low elastic recovery. However, the compositions of the present invention are not free-flowing fluids (i.e., liquids) above their softening points. That is, the compositions of the present invention display appreciable mass flow under moderate (e.g., hand) pressure, but not liquid flow above their softening points.

Typically, elastic and viscous dynamic moduli of hardenable compositions of the present invention vary over a wide range. Furthermore, the hardenable compositions are typically largely free from tack. Preferably, the elastic dynamic modulus (i.e., elastic modulus) G' is at least about 100 kilopascals (kPa), more preferably, at least about 200 kPa, and most preferably, at least about 1000 kPa, at a frequency of about 0.005 Hz. Preferably, the elastic modulus G' is no greater than about 50,000 kPa, more preferably, no greater than about 10,000 kPa, and most preferably, no greater than about 5000 kPa, at a frequency of about 0.005 Hz. Preferably, the viscous dynamic modulus (i.e., viscous modulus) G" is at least about 50 kPa, more preferably, at least about 200 kPa, and most preferably, at least about 1000 kPa, at a frequency of about 0.005 Hz. Preferably, the viscous modulus G" is no greater than about 50,000 kPa, more preferably, no greater than about 10,000 kPa, and most preferably, no greater than about 5000 kPa, at a frequency of about 0.005 Hz.

The desired self-supporting (i.e., free-standing) structure of hardenable compositions of the present invention can be maintained by creating a morphology that includes a noncovalent structure, which may be a three-dimensional network (continuous or discontinuous) structure. This can result from the use both a semi-crystalline resin component and one or more fillers comprising nanoclusters.

With the appropriate initiator system, e.g., a free radical photoinitiator, hardenable compositions of the present invention can be hardened (e.g., cured) to form the desired product. Preferably, the resultant hardened composition (i.e., the hardened structure) has a flexural strength of at least about 25 megapascals (MPa), more preferably, at least about 40 MPa, even more preferably, at least about 50 MPa, and most preferably, at least about 60 MPa.

For certain applications (e.g., crowns), the resultant hardened composition is an enamel-like solid, preferably having a compressive strength of at least about 100 MPa.

For certain applications (e.g., crowns), the resultant hardened composition is an enamel-like solid, preferably having a flexural modulus of at least about 1000 MPa. Further, the flexural strength is preferably at least 80 MPa. The flexural modulus is typically no greater than 15,000 MPa. Further, the flexural strength is typically no greater than 200 MPa.

Hardenable compositions of the present invention include a (e.g. free-radically) polymerizable resin system. The resin system includes one or more hardenable organic resins capable of forming a hardened material having sufficient strength and hydrolytic stability to render them suitable for use in the oral environment.

As used herein, a resin includes one or more monomers, oligomers, and/or polymerizable polymers, including combinations thereof. Although, in this context oligomers and polymers are both used, the terms "polymer" and "polymeric" are used herein to refer to any materials having 2 or more repeat units, thereby encompassing oligomers. Thus, unless otherwise specified, polymers include oligomers. Furthermore, the term polymer is used herein to encompass both homopolymers and copolymers, and the term copolymer is used herein to encompass materials with two or more different repeat units (e.g., copolymers, terpolymers, tetrapolymers).

A preferred organic resin is hardenable (e.g., polymerizable and/or crosslinkable), preferably by a free radical mechanism, and includes monomers, oligomers, and/or polymers. The resin system includes a reactive component (i.e., a component capable of polymerizing and/or crosslinking), which may or may not be crystalline. Resin systems that include noncrystalline reactive components may optionally include a crystalline component, which may or may not be reactive.

Preferably, at least some of the resin components include ethylenic unsaturation and are capable of undergoing (free-radical) addition polymerization. A suitable resin preferably includes at least one ethylenically unsaturated monomer (i.e., includes at least one carbon-carbon double bond).

The polymerizable resin of the dental composition described herein comprises at least one multi-(meth)acrylate aromatic monomer. The selection of components of the polymerizable resin and the concentration of such are generally chosen to minimize polymerization shrinkage. The dental composition described herein typically comprises at least one di-(meth)acrylate aromatic monomer The polymerization shrinkage can be determined via various methods such as Watts Shrinkage that measure the volumetric change after curing. Preferred low volume shrinkage (e.g. filled) dental compositions (useful for restorations such as fillings and crowns) as described herein typically exhibit a Watts Shrinkage of less than 2.5%. In favored embodiments, the Watts Shrinkage of the filled dental composition is less than 2.0%, or 1.9%, or 1.8%, or 1.7% or 1.6%.

In some embodiments, the multi-(meth)acrylate monomer is derived is a bisphenol A monomer such as 2,2-bis[4-(2-hydroxy-3-methacryloyloxypropoxy)phenyl]propane (Bis-GMA). A representative structure for BisGMA is depicted as follows, having a (i.e. calculated) molecular weight of about 512 g/mole:

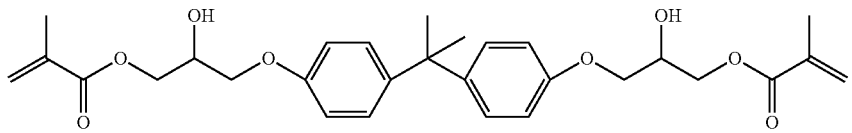 [SMILES: C=C(C)C(=O)OCC(O)COc1ccc(C(C)(C)c2ccc(OCC(O)COC(=O)C(=C)C)cc2)cc1]

Another class of monomers derived from bisphenol A are branched multi(meth)acrylate monomers (e.g. having pendant (meth)acrylate moities) such as described in WO2008/08288; incorporated herein by reference. These branched multi(meth)acrylate monomer may have the general formula and/or (ii) q=0 and $R^2$ represents —C(O)C(CH$_3$)=CH$_2$; m=1 to 5; n=0 to 5; p and q are independently 0 or 1; and $R^1$ and $R^2$ each independently represent H, —C(O)CH=CH$_2$, or —C(O)C(CH$_3$)=CH$_2$. In some embodiments, such as described in WO2008/08288, Y does not represent —NHCH$_2$CH$_2$— if (i) p=0.

However, branched multi-(meth)acrylate monomers (e.g. having pendant (meth)acrylate moities) having urethane linkages are described in EP2008636.

In favored embodiments, at least one $R^1$ or $R^2$ is —C(O)CH=CH$_2$, or —C(O)C(CH$_3$)=CH$_2$.

When the dental composition comprises a low shrinkage multi-(meth)acrylate monomer derived from bisphenol A, the dental restoration composition may be free of other multi-(meth)acrylate aromatic monomer such as biphenyl di(meth)acrylate monomers In other embodiments, the polymerizable resin system may be free monomer(s) derived from bisphenol A. For example, the low volume shrinkage monomer may be a di- or tri-(meth)acrylate isocyanurate monomer, such as described in U.S. Provisional Application Ser. No. 61/319,534, filed Mar. 31, 2010; incorporated herein by reference.

The polymerizable resin system optionally may comprise other polymerizable components. Examples of suitable polymerizable resin components include: mono-, di-, or poly-(meth)acrylates (including acrylates and methacrylates) such as methyl acrylate, methyl methacrylate, ethyl acrylate, isopropyl methacrylate, n-hexyl acrylate, stearyl acrylate, allyl acrylate, glycerol mono- and diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexaacrylate, bis(1-(2-acryloxy))-p-ethoxyphenyldimethylmethane, bis(1-(3-acryloxy-2-hydroxy))-p-propoxyphenyldimethyl-

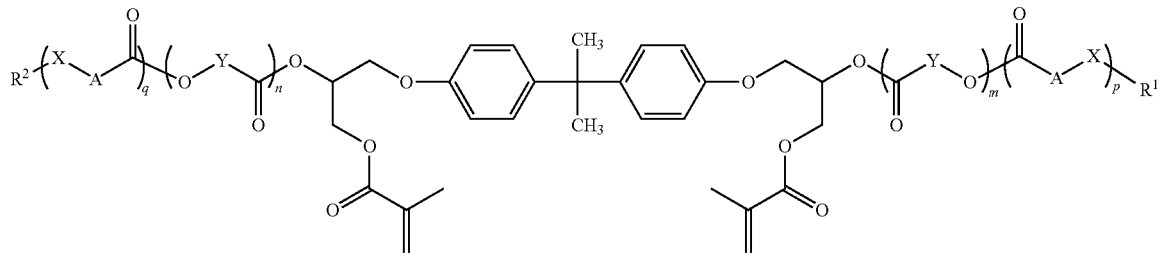

wherein each X independently represents an oxygen atom (O) or a nitrogen atom (N); Y and A each independently represent an organic group, and $R^1$ represents —C(O)C(CH$_3$)=CH$_2$, methane, tris(hydroxyethylisocyanurate)trimethacrylate, 2-hydroxyethyl methacrylate, 2-hydroxypropyl methacrylate, tetrahydrofurfuryl methacrylate, ethylene glycol dimethacrylate, triethylene glycol dimethacrylate, ethoxylated bisphenolA diacrylate, ethoxylated bisphenolA dimethacrylate (e.g. Bis-EMA6), polyethylene glycol dimethacrylate, the bis-acrylates and bis-methacrylates of polyethylene glycols of molecular weight 200-500, copolymerizable mixtures of acrylated monomers such as those of U.S. Pat. No. 4,652,274 (Boettcher et al.), and acrylated oligomers such as those of U.S. Pat. No. 4,642,126 (Zador et al.); unsaturated amides such as (meth)acrylamides (i.e., acrylamides and methacrylamides), methylene bis-acrylamide, methylene bis-methacrylamide, 1,6-hexamethylene bis-acrylamide, diethylene triamine tris-acrylamide, and beta-methacrylamidoethyl methacrylate, diacetone acrylamide, and diacetone methacrylamide; urethane (meth)acrylates; and vinyl compounds such as styrene, diallyl phthalate, divinyl succinate, divinyl adipate, and divinylphthalate. Mixtures of two or more such materials can be used if desired in the resin system.

In some embodiments, the dental restoration composition comprises a low shrinkage aromatic di(meth)acrylate monomer such as BisGMA in combination with one or more other free-radically polymerizable (e.g. methacrylate) monomers. In certain embodiments, the other hardenable components can include diurethane dimethacrylate (UDMA), triethyleneglycol dimethacrylate (TEGDMA), and ethoxylated bisphenol A dimethacrylate as described in U.S. Pat. No. 6,030,606 (Holmes), also referred to herein as "Bis-EMA6"; and 2,2-bis[4-(2-hydroxy-3-methacryloyloxypropoxy)phenyl]propane (Procrylate). In some embodiments, the dental restoration composition comprises BisGMA in combination with ethoxylated bisphenol A dimethacrylate and diurethane dimethacrylate.

The concentration of the other monomers (including the semi-crystalline resin as will subsequently be described) is generally no greater than 20 wt-% or 15 wt-% based on the total weight of the composition. In some embodiments, the concentration is less than 15 wt-%, or 14 wt-% or 13 wt-%. In some favored embodiments, the concentration is typically less than 12 wt-%, or 11 wt-%, or 10 wt-%. In other favored embodiments, the concentration is typically less than 9 wt-%, or 8 wt-%, or 7 wt-%, or 6 wt-%, or 5 wt-%. The inclusion of 1 wt-% or 2 wt-%, or 3 wt-% of other monomers that are lower in molecular weight than BisGMA may increase the rate of polymerization of the dental article or composition during curing.

Preferably, the total amount of the (organic) polymerizable resin system is at least about 10 wt-%, more preferably, at least about 12 wt-%, and most preferably, at least about 14 wt-%, based on the total weight of the composition. Preferably, the total amount of the resin system is no greater than about 30 wt-%, more preferably, no greater than about 25 wt-%. In favored embodiments, the total amount of polymerizable resin is less than 25 wt-%, or 24 wt-%, or 23 wt-%, or 22 wt-%, or 21 wt-%, or 20 wt-%.

The above-listed components are typically noncrystalline (i.e., amorphous). The polymerizable resin system also includes a crystalline component to impart the noncovalent three-dimensional structure for maintaining the initial preformed shape. This crystalline component may or may not have a reactive group capable of polymerizing (also including crosslinking). Preferably, the crystalline component is polymerizable. Preferably, the crystalline component is polymeric (including oligomeric). More preferably, the crystalline component is a polymerizable polymeric material.

By "crystalline" it is meant that the material displays a crystalline melting point at 20° C. or above when measured in the composition by differential scanning calorimetry (DSC). The peak temperature of the observed endotherm is taken as the crystalline melting point. The crystalline phase includes multiple lattices in which the material assumes a conformation in which there is a highly ordered registry in adjacent chemical moieties of which the material is constructed. The packing arrangement (short order orientation) within the lattice is highly regular in both its chemical and geometric aspects.

More specifically, the polymerizable resin system comprises a semi-crystalline component. A semi-crystalline component typically comprises long segments of polymer chains that appear in both amorphous and crystalline states or phases at 20° C. or above. The amorphous phase is considered to be a randomly tangled mass of polymer chains. The X-ray diffraction pattern of an amorphous polymer is a diffuse halo indicative of no ordering of the polymer structure. Amorphous polymers show softening behavior at the glass transition temperature, but no true melt or first order transition. A material in a semicrystalline state shows characteristic melting points, above which the crystalline lattices become disordered and rapidly lose their identity. The X-ray diffraction pattern of such "semicrystalline" materials generally is distinguished by either concentric rings or a symmetrical array of spots, which are indicative of the nature of the crystalline order.

The semi-crystalline material is preferably derived from a polyester polymer comprising polycaprolactone repeat units. Polycaprolactone (PCL) homopolymer is a biodegradable polyester with a low melting point of about 60° C. and a glass transition temperature of about −60° C. PCL can be prepared by ring opening polymerization of ε-caprolactone using a catalyst such as stannous octanoate, forming repeat units of polycaprolactone having the general structure:

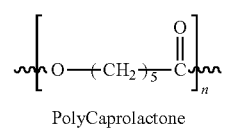

PolyCaprolactone

The polycaprolactone polymers utilized herein are typically derived from linear polyester diols derived from caprolactone. One suitable linear polyester diols derived from caprolactone is Capa™ 2125, reported to have a hydroxyl values of 90 mg KOH/g.

In a favored embodiment, the free-radically polymerizable semi-crystalline resin utilized herein is derived from a polycarpolactone diol having a melt point of 35° C. to 45° C.

The primary hydroxyl groups are then reacted with a hydroxyl reactive (meth)acrylate compound such as an isocyanatoalkyl (meth)acrylate (e.g. 2-isocyanatoethyl methacrylate), methacryloyl chloride, or methacrylic anhydride to convert the hydroxyl group to free-radically polymerizable (e.g. (meth)acrylate) groups.

The free-radically polymerizable semi-crystalline component (e.g. the reaction product of polycaprolactone diol and isocyanatoalkyl (meth)acrylate) has a number average molecular weight (as measured according to the test method described in the examples) of no greater than 3,000 g/mole. In some embodiments, the number average molecular weight of the free-radically polymerizable semi-crystalline component is no greater than 2700 g/mole or 2600 g/mole or 2500 g/mole. The molecular weight is typically at least about 400 g/mol or 500 g/mol. In some favored embodiments, the semi-crystalline component has a number average molecular weight of at least 1000 g/mole.

The concentration of the semi-crystalline component(s) (e.g. polycaprolactone (meth)acrylate resin) in the total dental composition is at least about 0.5 wt-% or 1.0 wt-%, based on the total weight of the composition. Preferably, the total amount of semi-crystalline component is no greater than about 15 wt-%. In some embodiments, the total amount of semi-crystalline components is no greater than 10 wt-% or 8 wt-%. In some embodiments, the concentration of semi-crystalline component ranges from about 0.8 wt-% to about 2.5 wt-%. In other embodiments, the concentration of semi-crystalline component is at least 3.0 or 3.5 wt-% and typically no greater than 6.0 wt-%, or 5.5 wt-%, or 5.0 wt-%.

In some favored embodiments, the semi-crystalline component is the sole crystalline component of the dental composition. In this embodiment, the dental composition is free of crystalline components that are not semi-crystalline. In other embodiments, the semi-crystalline component may be employed in combination with other crystalline components. In this later embodiment, the semi-crystalline component is the major crystalline component, i.e. at least 50%, 60%, 70%, 80%, 90% or greater of the total concentration of crystalline components. When a crystalline component is employed in combination with a semi-crystalline component, the crystalline component may also have a number average molecular weight of no greater than 2,000 g/mol. Alternatively, the crystalline component may also have a greater number average molecular weight, ranging up to than 5,000 g/mol or 10,000 g/mole. The total amount of crystalline and semi-crystalline component is typically within the range previously described with respect to the concentration of semi-crystalline component(s) in the dental composition The crystalline monomers suitable for use in the resin system include monomers containing urethane, ether, ester, amide, imide groups, or combinations thereof. Preferred crystalline monomers contain reactive groups capable of polymerizing and/or crosslinking. Especially preferred are monomers with a reactive functionality greater than one.

The crystalline polymers (including oligomers) suitable for use in the resin system can have crystalline main chain (i.e., linear) or pendant (i.e., side chain) segments. Preferred materials also contain reactive groups capable of polymerizing and/or crosslinking. Especially preferred are crystalline oligomers or prepolymers with a reactive functionality of at least two.

Examples of suitable crystalline materials having crystallizable main chain or backbone segments include, but are not limited to, polyesters (including polycaprolactones), polyethers, polythioethers, polyarylalkylenes, polysilanes, polyamides, polyolefins (preferably, formed from lower, e.g., $C_2$-$C_3$, olefins), and polyurethanes. Various crystalline material are described in U.S. Pat. Nos. 7,674,850 and 7,816,423; incorporation herein by reference.

The crystalline components, including the semi-crystalline component crystallizes at least in part above room temperature (i.e., 20° C. to 25° C.). Such crystallinity, that may be provided by the aggregation of crystallizable moieties present in the component (e.g., when the component is a polymer, in the backbone (i.e., main chain) or pendant substituents (i.e., side chains) of the component), can be determined by well known crystallographic, calorimetric, or dynamic/mechanical methods. For the purposes of the present invention, this component imparts to the resin system at least one melting temperature ($T_m$) as measured experimentally (for example by DSC) of greater than about 20° C. Preferably, this component imparts a $T_m$ to the resin system of about 30° C.-100° C. If more than one crystalline material is used in the crystalline component, more than one distinct melting point may be seen.

The polymerizable resin system may optionally comprise an organogelator as described in US2009/0305196. However, the desired properties can be achieved when the dental composition is free of organogelator.

The dental compositions described herein comprise a major amount of filler. The filler is generally (non-toxic) suitable for use in the mouth. The filler can be radiopaque, radiolucent, or nonradiopaque.

Inorganic fillers, as used in dental applications, are typically ceramic in nature.

Examples of suitable inorganic fillers are naturally occurring or synthetic materials such as quartz, nitrides (e.g., silicon nitride), glasses derived from, for example Ce, Sb, Sn, Zr, Sr, Ba, or Al, colloidal silica, feldspar, borosilicate glass, kaolin, talc, titania, and zinc glass, zirconia-silica fillers; and low Mohs hardness fillers such as those described in U.S. Pat. No. 4,695,251 (Randklev). The nanoscopic filler particles are typically composed of silica, alumina, zirconia, titania, or mixtures of these materials with each other.

The filler system comprises nanoscopic fillers. Due to their small size, high surface area, and associated hydrogen bonding, these materials are known to assemble into aggregated networks. Materials of this type ("nanoscopic" materials) have average primary particle sizes (i.e., the largest dimension, e.g., diameter, of unaggregated material) of less than 200 nanometers (nm). Preferably, the nanoscopic particulate material has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2$/g), more preferably, at least about 50 $m^2$/g, and most preferably, at least about 100 $m^2$/g.

The filler system comprises nanoparticles in the form of nanoclusters, i.e. a group of two or more particles associated by relatively weak intermolecular forces that cause the particles to clump together, even when dispersed in a hardenable resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Mitra et al.); incorporated herein by reference The dental compositions described herein generally comprise at least 40 wt-%, or 45 wt-% or 50 wt-% of (e.g. silica/zirconia) nanoclusters. The concentration of (e.g. silica/zirconia) nanoclusters is typically no greater than about 65 wt-%.

In favored embodiments, the dental composition comprises a (i.e. non-associated) nanoscopic inorganic filler in combination with the (e.g. silica/zirconia) nanoclusters. Such nanoscopic inorganic filler typically comprises silica nanoparticles.

The dental compositions described herein generally comprise at least 10 wt-% or 15 wt-% of (e.g. silica) nanoscopic filler(s). The concentration of (e.g. silica) nanoscopic filler is typically no greater than about 40 wt-%.

Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1034A, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols which can be used in preparing the fillers of the invention are available commercially having different colloid sizes, see Surface &

Colloid Science, Vol. 6, ed. Matijevic, E., Wiley Interscience, 1973. Preferred silica sols for use making the fillers of the invention are those which are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 2327.

The nano-sized filler may also include fumed silica. In some embodiments, the fumed silica is present in an amount ranging from 1 wt-% or 2 wt-% up to 5 wt-%.

Preferably, the total amount of nanoscopic filler (including the nanocluster) is greater than 50 wt-%, more preferably, greater than 60 wt-%, and most preferably, greater than 70 wt-%, based on the total weight of the composition. Preferably, the total amount of filler system is no more than about 95 wt-%, and more preferably, no more than about 80 wt-%, based on the total weight of the composition.

The filler system can optionally include other fillers. Such optional other fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Particulate filler is finely divided and has an average particle size (preferably, diameter) of less than about 10 micrometers (i.e., microns). The filler can have a unimodal or polymodal (e.g., bimodal) particle size distribution.

The optional filler can be an inorganic material, as previously described. It can also be a crosslinked organic material that is insoluble in the polymerizable resin, and is optionally filled with inorganic filler. Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Mixtures of these fillers can also be used, as well as combination fillers made from organic and inorganic materials.

The surfaces of the inorganic filler particles are typically treated with a surface treatment, such as a silane-coupling agent, in order to enhance the bond between the filler and the resin system. The coupling agent may be functionalized with reactive curing groups, such as acrylates, methacrylates, and the like.

Filler particles composed of silica, alumina, zirconia, titania, or mixtures of these materials are commonly hydrophilic, due to the presence of surface hydroxyl groups. However, the filler materials are typically modified by treatment with appropriate agents, to render the surface increasingly hydrophobic.

The nanoscopic filler (including the nanoclusters) are typically surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formula:

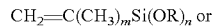

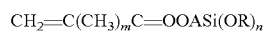

wherein m is 0 or 1,
R is an alkyl group having 1 to 4 carbon atoms,
A is a divalent organic linking group, and
n is from 1 to 3.

Preferred coupling agents include gamma-methacryloxypropyltrimethoxysilane, gamma-mercaptopropyltriethoxysilane, gamma-aminopropyltrimethoxysilane, and the like.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such particle size, particle type, modifier molecular wt, and modifier type. In general it is preferred that approximately a monolayer of modifier is attached to the surface of the particle.

In some embodiments, the fumed silica does not comprise surface modification.

The compositions of the present invention also contain an initiator system, i.e., one initiator or a mixture of two or more initiators, which are suitable for hardening (e.g., polymerizing and/or crosslinking) of the resin system, as described in U.S. Pat. Nos. 7,674,850 and 7,816,423. The initiators are preferably free radical initiators, which may be activated in a variety of ways, e.g., heat and/or radiation. Thus, for example, the initiator system can be a thermal initiator system (e.g., azo compounds and peroxides), or a photoinitiator system. Preferably, the initiator system includes one or more photoinitiators. More preferably, the initiator system includes at least one photoinitiator active in the spectral region of about 300 nanometers (nm) to about 1200 nm and capable of promoting free radical polymerization and/or crosslinking of ethylenically unsaturated moieties upon exposure to light of suitable wavelength and intensity. A wide variety of such photoinitiators can be used. The photoinitiator preferably is soluble in the resin system. Preferably, they are sufficiently shelf stable and free of undesirable coloration to permit storage and use under typical dental operatory and laboratory conditions. Visible light photoinitiators are preferred.

One type of suitable initiator (i.e., initiator system) is described in U.S. Pat. No. 5,545,676 (Palazzotto et al.), which includes a three component or ternary photoinitiator system. This system includes an iodonium salt, e.g., a diaryliodonium salt, which can be a simple salt (e.g., containing an anion such as $Cl^-$, $Br^-$, $I^-$, or $C_2H_5SO_3^-$) or a metal complex salt (e.g., containing $SbF_5OH^-$ or $AsF_6^-$). Mixtures of iodonium salts can be used if desired. The second component in this ternary photoinitiator system is a sensitizer, which is capable of light absorption within the range of wavelengths of about 400 nm to about 1200 nm. The third component in this ternary photoinitiator system is an electron donor and includes amines (including aminoaldehydes and aminosilanes or other amines as described for the first initiator system), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid.

Examples of sensitizers suitable for use in a ternary photoinitiator system include ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes, and pyridinium dyes. Ketones (e.g., monoketones or alpha-diketones), ketocoumarins, aminoarylketones, and p-substituted aminostyryl ketone compounds are preferred sensitizers. Examples of particularly preferred visible light sensitizers include camphorquinone, glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione, 3,3,18,18-tetramethyl-1,2-cyclooctadecanedione, dipivaloyl, benzil, furil, hydroxybenzil, 2,3-butanedione, 2,3-pentanedione, 2,3-hexanedione, 3,4-hexanedione, 2,3-heptanedione, 3,4-heptanedione, 2,3-octanedione, 4,5-octanedione, and 1,2-cyclohexanedione. Of these, camphorquinone is the most preferred sensitizer.

Preferred visible light-induced initiators include camphorquinone combined with a suitable hydrogen donor (e.g., an amine such as those described above for the first initiator system), and optionally a diaryliodonium simple or metal complex salt, chromophore-substituted halomethyl-s-triazine, or halomethyl oxadiazole. Particularly preferred visible light-induced photoinitiators include combinations of an alpha-diketone, e.g., camphorquinone with additional hydrogen donors, and optionally a diaryliodonium salt, e.g., diphenyliodonium chloride, bromide, iodide or hexafluorophosphate.

Preferred ultraviolet light-induced polymerization initiators include ketones, such as benzyl and benzoin, acyloins, and acyloin ethers. Preferred ultraviolet light-induced polymerization initiators include 2,2-dimethoxy-2-phenylacetophenone available under the trade designation IRGACURE 651 and benzoin methyl ether (2-methoxy-2-phenylacetophenone), both from Ciba Speciality Chemicals Corp., Tarrytown, N.Y.

Various other initiators are known in the art, such as described in U.S. Pat. Nos. 7,674,850 and 7,816,423.

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least about 0.01 wt-%, more preferably, at least about 0.03 wt-%, and most preferably, at least about 0.05 wt-%, based on the weight of the composition. Preferably, the initiator system is present in a total amount of no more than about 10 wt-%, more preferably, no more than about 5 wt-%, and most preferably, no more than about 2.5 wt-%, based on the weight of the composition.

The compositions of the invention may optionally contain a surfactant system, i.e., one surfactant or a mixture of two or more surfactants. These surfactants, when used in small amounts may interact with other components of the composition, such as an inorganic filler material, to enhance the formation of a noncovalent three-dimensional structure. Such surfactants can be nonionic, anionic, or cationic. The surfactant(s) can be copolymerizable with the resin system or non-copolymerizable. A consideration in the choice of a surfactant that can be used is the degree to which the ingredients of the system are able to participate in hydrogen bonding. The desired properties can be achieved when the dental composition is free of surfactant.

The composition may additionally include optional agents such as colorants (e.g., pigments conventionally used for shade adjustment), flavorants, medicaments, stabilizers (such as BHT), viscosity modifiers, and the like. Such agents may optionally include reactive functionality so that they will be copolymerized with the resin.

The combination of semi-crystalline resin and nanocluster filler system, as described herein, renders the dental composition, dental articles, and methods improved properties.

The dental restoration composition and articles described herein has been found to exhibit improved properties.

In some embodiments, the cured compositions and cured articles exhibited improved staining resistance. In some embodiments, the change in color (i.e. Delta E*) may be 1 or 2 units lower relative to a control (e.g. CE-1) when tested in a 15% coffee solution at 37° C. for 3 days. In other embodiments, the change in color may be 3, 4, 5, 6, or 7 units lower relation to a control (e.g. CE-2).

In some embodiments, the uncured preformed articles exhibited improved handling, i.e. "good handling" as determined by the test method described in the forthcoming examples.

In some embodiments, the cured compositions and cured articles exhibited improved 3-body wear as determined by the test method described in the forthcoming examples. In favored embodiments, the wear ratio was 0.5 or less. The wear ratio is typically at least 0.1 or 0.2.

The compositions of the present invention can be shaped (e.g., molded) into a variety of forms like three-dimensional shapes, preformed sheets, arch-shaped trays, ropes, buttons, woven, or non-woven webs, and the like. The composition can be shaped (to form a first shape) in a variety of ways including, for example, extruding, injection molding, compression molding, thermoforming, vacuum forming, pressing, calendering, and web processing using rollers. Typically, a semi-finished shape is formed using a mold with a positive and negative impression.

The shaped articles can be sold individually or in multiple units, preferably packaged in a way that protects them from heat and/or light that can activate the initiator system contained in the composition.

Generally, a preformed article of appropriate size and shape (the first shape) is selected and custom shaped at a temperature of about 15° C. to 38° C. (preferably, about 20° C. to 38° C., which encompasses typical room temperatures and body temperatures, and more preferably, at room temperature). This shaping can be done by a variety of methods including applying pressure with fingers or an instrument of choice (e.g., hand operation of dental composite instrument), trimming, cutting, sculpting, grinding, etc. Once the desired custom shape has been achieved, the article is hardened (e.g., cured) by exposing it to heat/radiation to cause activation of the initiator system. This can be done either in a single step, or in multiple steps with successive steps of custom shaping being done in-between. One or more of these steps can be carried out in an oxygen-free inert atmosphere or in vacuum. After the final shaping and hardening steps, the hardened article can be further modified in shape by grinding, trimming, etc., if desired. Once the final custom shape of the article has been obtained, it can be polished, painted, or otherwise surface treated, if required for the intended application. Preferably, the final custom shaped articles prepared from the compositions of the present invention do not need an additional veneering material (e.g., a second material that provides a desired appearance or property). The intended application may require mounting, bonding, or otherwise attaching the custom shaped cured article to a second object adhesively, mechanically, or by combination of both.

For the preparation of a (e.g. provisional or permanent) dental crown, an appropriate shape and size of a preformed crown is selected and the preformed crown is seated on the prepared tooth to determine the extent of trimming and shaping required, optionally making marks on the crown. The preformed crown is removed from the mouth, the required shape and size adjustments are made by cutting, trimming, shaping, etc., and then re-seated on the tooth preparation where additional shape adjustments are made to provide optimum custom fit, including gingival, lateral, and occlusal fit. The preformed and reshaped crown can then be hardened, typically by exposing it to a dental curing light for a few seconds, if desired, while in the mouth, and then removing it carefully from the mouth and exposing it for final cure to a curing light in a cure chamber, optionally in combination with heat. Alternatively, the crown can also be completely cured in the mouth by irradiating it with a dental curing light. Final adjustments are made by grinding, trimming, etc., if required, and the finished crown is polished and cleaned. The finished crown can then be cemented as is or lined with a suitable resin material prior to placement in the mouth.

The hardenable, self-supporting structures (e.g., dental products) of this invention can be prepackaged either individually or as an ensemble. Such packaging material should protect these products from conditions that would activate the initiator system and thus cause premature hardening, e.g., such as could result from exposure to light in the case of a photoinitiator. In addition, the packaging material optionally conforms to the surfaces of the product, thereby providing additional mechanical strength in order to resist damage during shipping. For example, a preformed crown or tray could be packaged in a layer of polyethylene on all sides. The polyethylene provides a mechanical structure and can be sealed to avoid contact with water. If the polyethylene were filled with an appropriate dye, e.g., carbon black, incident light would be absorbed before it could reach the enclosed product. If such a packaging layer is somewhat rigid, and if the packaging material is shaped similar to the preformed article of the invention, then the packaging could enhance the dimensional stability of the preformed product during shipment and storage. In certain cases, the packaging may thus form an integral part of the product system.

The invention is also useful in a number of preformed orthodontic applications as described in WO 03/015720; incorporated herein by reference. The composition of the invention can be shaped to a desired configuration in vivo and then hardened in place in the oral cavity. Alternatively, the composition can be shaped to a desired configuration outside of the oral cavity using, if desired, a model of the patient's tooth structure. When the composition is shaped outside of the oral cavity, the composition is preferably hardened before placement in the oral cavity.

EXAMPLES

The following examples are given to illustrate, but not limit, the scope of this invention. Unless otherwise indicated, all parts and percentages are by weight.

| Generic Chemical Description | Cass Number | Supplier |
|---|---|---|
| Component Utilized in the Preparation of the Hardenable Dental Composition | | |
| IEM (2-isocyanatoethyl methacrylate) | 30674-80-7 | Showa Denko, Japan |
| BisGMA (Bisphenol A diglycidyl ether methacrylate) | 1565-94-2 | Sigma-Aldrich, St. Louis, MO |
| BisEMA-6 (six-mole ethoxylated bisphenol A dimethacrylate, Sartomer CD-541) | | Sartomer Co., Inc., Exton, PA |
| TEGDMA (triethyleneglycol dimethacrylate) | | Sartomer |
| TPEG 990 (polymer of ethylene oxide) | | Dow Chemical Co. |
| Procrylate (2,2-bis-4-(3-hydroxy-propoxy-phenyl)propane dimethacrylate) | 27689-12-9 | Prepared as described in WO 2006/020760 |
| UDMA (diurethane dimethacrylate) | 72869-86-4 | Dajac Laboratories, Trevose, PA |
| CAPA2125 | 36890-68-3 | Solvay Chemical Co., Warrington, UK |
| CAPA2205 | 36890-68-3 | Solvay Chemical Co., Warrington, UK |
| CAPA2200A | | Solvay Chemical Co., Warrington, UK |
| Tone0230 | 36890-68-3 | Dow Chemical Company, Midland, Michigan |
| BHT (2,6-di-tert-butyl-4-methylphenol) | 128-37-0 | Sigma-Aldrich |
| Tinuvin R 796 (benzotriazole polymerizable UV stabilizer) | | Ciba Specialty Chemicals, Tarrytown, NY |
| Dibutyltin Dilaurate | | Sigma-Aldrich |
| Components of Photoinitiator Package | | |
| CPQ (camphorquinone) | | Sigma-Aldrich |
| EDMAB (ethyl 4-(N,N-dimethylamino) benzoate) | | Sigma-Aldrich |
| DPIHFP (diphenyl iodonium hexafluorophosphate) | | Alpha Aesar, Ward Hill, MA |
| Pigments | | |
| Red pigment dispersion (viscous dispersion containing red iron III oxide pigment) | | |
| White pigment dispersion (viscous dispersion containing rutile titanium dioxide pigment) | | |
| Black pigment dispersion (viscous dispersion containing a black iron oxide (Fe3O4) pigment) | | |
| Yellow pigment dispersion (viscous dispersion containing a yellow iron III oxide pigment) | | |
| Inorganic Fillers | | |
| Zr/Si nanocluster - Refers to silane-treated zirconia/silica nanocluster filler prepared essentially as described in U.S. Pat. No. 6,730,156 (Preparatory Example A (line 51-64) and Example B (column 25 line 65 through column 26 line 40) | | |
| 20 nm Silica Nanomer - Refers to silane-treated nano-sized silica having a nominal particle size of approximately 20 nanometers, prepared essentially as described in U.S. Pat. No. 6,572,693 B1, (column 21, lines 63-67 for Nanosized particle filler, Type #2) | | |
| Cabosil M5 - Refers to a fumed silica available under the trade designation CAB-O-SIL M-5 from Cabot Corp., Boston, MA | | |
| S/T Filler - Refers to silane treated zirconia silica filler, prepared as described in Columns 15 and 16 of U.S. Pat. No. 6,624,211 | | |

Preparation of Polycaprolactone Di(Meth)Acrylates

To a 32 oz. glass jar was added about 50 grams of polycaprolactone diol and about 0.04 g BHT, and this was heated in an oil bath to 60° C. After melting of all the solid polycaprolactone and under magnetic stirring, 2 molar equivalent of IEM (about 7.8 g) was added over 15 minutes. A drop (~0.02 g) of dibutyltin dilaurate (Aldrich) was added to the mixture. This reaction was continued at 60° C. for 12 hours. The resulting white solids were characterized with IR and NMR and confirmed to be the respective polycaprolactone IEMs.

Gel Permeation Chromatography (GPC) Test

Approximately 25.0 mgs of each sample was added to 10.0 ml of tetrahydrofuran. The sample solutions were shaken overnight and were filtered with a 0.25 micron Teflon syringe filter The GPC analysis was as follows—

| Instrument | Waters Inc. 2695 Separations Module |
|---|---|
| Column set | Jordi Associates 500A (50 cm) |
| Eluent | THF |
| Injection | 100 μL |
| Detector | Shimadzu RID-10A Refractive Index Detector |
| Temperature | 35° C. |

The molecular weight calculations were based upon a calibration made of narrow dispersity polystyrenes ranging in molecular weight from 5.95E+04 down to 266. The actual calculations were completed with Cirrus GPC software from Polymer Labs.

The number average molecular weight (Mn) of the polycaprolactone di(meth)acrylate prepared from the polycaprolactone diol "CAPA 2125" was determined to be 2270 g/mole according to the test method just described.

The number average molecular weight (Mn) of the polycaprolactone di(meth)acrylates of the comparative examples was also determined according to the same test method. The number average molecular weight (Mn) of the polycaprolactone di(meth)acrylate prepared from the polycaprolactone diol "CAPA 2205" was determined to be 3590 g/mole. The number average molecular weight (Mn) of the polycaprolactone di(meth)acrylate prepared from the polycaprolactone diol "Tone 230" was determined to be 2200 g/mole. The number average molecular weight (Mn) of the polycaprolactone di(meth)acrylate prepared from the polycaprolactone diol "CAPA 2200A" was determined to be 2790 g/mole.

Preparation of Curable Dental Restoration Compositions

The components listed in Table 1 were mixed in the following way: pigments were initially mixed with the resin components until uniform, then the filler was added and the final composition was mixed until uniform.

Examples (Ex) and Comparative Examples (CE) (wt %)

| | EX1 | EX2 | EX3 | EX4 | EX5 | CE1 | CE2 |
|---|---|---|---|---|---|---|---|
| BisGMA | 3.9189 | 3.7126 | 3.3001 | 14.4383 | 3.3001 | | 10.5498 |
| BisEMA6 | 6.8671 | 6.4972 | 5.7752 | 1.0313 | 5.7752 | | |
| TEGDMA | 0.9798 | 0.9283 | 0.8250 | | 0.8250 | | |
| UDMA | 3.9189 | 3.7126 | 3.3001 | 1.0313 | 3.3001 | 12.9490 | |
| Procrylate | 3.9189 | 3.7126 | 3.3001 | | 3.3001 | 4.3160 | |
| CAPA2125-IEM | 1.0226 | 2.0629 | 4.1257 | 4.1257 | | | |
| CAPA2205-IEM | | | | | | 4.3160 | |
| CAPA2200A-IEM | | | | | 4.1257 | | |
| Tone 230-IEM | | | | | | | 9.0960 |
| TPEG990 | | | | | | | 0.6000 |
| SiO$_2$/ZrO$_2$ nanocluster | 55.7979 | 55.7979 | 55.7979 | 57.2451 | 55.7979 | 44.6400 | |
| 20 nm Silica Nanomer | 19.5497 | 19.5497 | 19.5497 | 19.0817 | 19.5497 | 29.7600 | |
| Cabosil M5 | 3.1392 | 3.1392 | 3.1392 | 2.1600 | 3.1392 | 3.0890 | 2.1698 |
| S/T Filler | | | | | | | 76.7302 |
| Red Pigment Dispersion | 0.0100 | 0.0100 | 0.0100 | 0.0100 | 0.0100 | 0.0040 | 0.0117 |
| White Pigment Dispersion | | | | | | 0.0400 | 0.1065 |
| Black Pigment Dispersion | | | | | | 0.0040 | 0.0002 |
| Yellow Pigment Dispersion | 0.0430 | 0.0430 | 0.0430 | 0.0430 | 0.0430 | 0.0480 | 0.0613 |
| CPQ | 0.0610 | 0.0610 | 0.0610 | 0.0610 | 0.0610 | 0.0610 | 0.0345 |
| EDMAB | 0.2240 | 0.2240 | 0.2240 | 0.2240 | 0.2240 | 0.2240 | 0.2032 |
| DPIHFP | 0.1790 | 0.1790 | 0.1790 | 0.1790 | 0.1790 | 0.1790 | 0.1016 |
| BHT | 0.0340 | 0.0340 | 0.0340 | 0.0340 | 0.0340 | 0.0340 | 0.0305 |
| Tinuvin R 976 | 0.3360 | 0.3360 | 0.3360 | 0.3360 | 0.3360 | 0.3360 | 0.3048 |

Flexural Strength Test

Test Method:

Flexural Strength was tested by following the procedure described in International Standard ISO 4049-2009, entitled "Dentistry—Polymer-based filling, restorative and luting materials".

| Material | Flexural Strength MPa | Standard Deviation | Flexural Modulus MPa | Standard Deviation |
|---|---|---|---|---|
| Example 3 | 125.7 | 11.0 | 9177 | 1239 |
| Example 4 | 110.8 | 27.4 | 9647 | 1057 |
| CE-1 | 124.3 | 11.0 | 9341 | 896 |
| CE-2 | 113.9 | 12.8 | 6204 | 723 |

Watts Shrinkage Test

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample as follows:

| Material | Total Shrinkage % |
|---|---|
| EX1 | 2.14 |
| EX2 | 2.08 |
| EX3 | 2.11 |
| EX4 | 1.55 |
| CE-1 | 2.07 |
| CE-2 | 1.65 |

Staining Test

Staining Disk Preparation

Samples (approximately 10 grams) of the dental compositions were pressed to a thickness of approximately 1.1 millimeters (between 2 pieces of silicone release paper), using a hydraulic press (available from Carver Inc., Wabash, Ind.) at approximately 60° C. Each pressed sample was then stored at room temperature for 7 days, after which a 14 mm diameter disc was cut and placed in a 1 mm thick by 15 mm diameter split mold, sandwiched between 2 pieces of 1 mil polyester film available from DuPont under the trade designation "Mylar". This was then placed between 2 steel plates, and pressed in the above hydraulic press at 37° C. for 2 minutes under 1000 psi ($6.9 \times 10^6$ Pa). The polyester film sandwiched sample was then taken out of the hydraulic press, covered with a 1 mm thick, 50 mm×75 mm glass microscope slide (VWR Catalog #374-1407) over the polyester film, and light cured for 50 seconds by using VISILUX Model 2500 dental curing light (3M ESPE). After that, the other side was also cured for 50 seconds through a glass microscope slide. With the polyester films still present, the dental composite disc was conditioned in a 37° C. oven for 15 minutes. This sample disc was then stored in 37° C. deionized water before staining test.

Coffee Solution

A 15% coffee solution was prepared by adding 15 g of Folgers Classic Roast Instant Coffee Crystals to 85 g of 80° C. de-ionized water, mixing well, and then letting it cool down to 37° C. or less. (coffee crystals commercially available from The Folger Coffee Company, Cincinnati, Ohio 45202). Two discs were used from each formulation for the staining test. The CIELAB color of each disc was measured before the staining test as follows. A spectrophotometer obtained from HunterLab, Reston, Va. under the trade designation "UltraScan XE" in small area view mode with RSIN (reflectance specular included) was used to measure the L*, a*, and b* values. After the initial color measurements, the dental composite discs were placed in 15% coffee solution at 37° C. for 3 days. The stained discs were then rinsed with de-ionized water, and the color of the stained discs was measured again. The staining resistance is reported as Delta E* as defined below:

$$\text{Delta } E^* = [(L_0^* - L_1^*)^2 + (a_0^* - a_1^*)^2 + (b_0^* - b_1^*)^2]^{1/2}$$

wherein each 0 represents the initial values and each 1 represents the values after conditioning the hardened dental composition in the indicated test solution.

The test results are as follows:

| Staining - 15% coffee staining data (37° C./3 days) | | |
|---|---|---|
| Materials | Delta E* | Standard Deviation |
| EX1 | 5.50 | 0.17 |
| EX2 | 5.37 | 0.41 |
| EX3 | 6.15 | 0.01 |
| EX4 | 6.72 | 0.83 |
| CE-1 | 8.61 | 0.78 |
| CE-2 | 12.76 | 1.37 |

Crown Formation and Handling Assessment

Crowns were prepared by a two-stage process, analogous to that described in patent application US2005/100868. Samples of each paste to be tested were injected into a cavity lined with an ethylene-vinyl acetate (EVA) copolymer film, containing ~19% vinyl acetate. This sample of paste was transferred to a second multi-part mold, covered with a second polyethylene film, and compression molded to form a hollow crown shape. This mold was in the form of a symmetric model lower first molar. The resulting formed crown had a mesial-distal dimension of approximately 10.6 mm.

The above prepared crowns were conditioned/aged at different Temperature/Humidity environment to mimic storage condition change with the season, including a 23° C./15% RH dry environment.

The materials were evaluated by an experienced dentist customizing the crowns formed of the materials on a prepared artificial tooth in a Columbia Dentoform R862 Typodont, at the #31 position. The Typodont tooth was modified to have a shoulder preparation. The crown was wet with water, manipulated by hand to obtain an initial assessment of the handling, and adapted to the preparation in the Typodont. Overall acceptability of the handling was assessed based on ability to trim, adjust, and smooth the crown before cure.

After 2 weeks of aging at 23° C./15% RH dry environment, the crown handling results are shown in the forthcoming table.

3 Body Wear

Samples were compared with Comparative Example 2 (CE2) in 3-body wear testing generally according to the ACTA method described by P. Pallav, C. L. Davidson, and A. J. DeGee in J Pros Dent 59 (1988) (4), pp. 426-429. The procedure was modified by excluding sodium azide from the wear media, and by preparing the wear wheel initially by machining rather than grinding on the ACTA-wear machine. Wear rate was measured by measuring the wear depth at 6 intervals, fitting a line by the least-squares method, and generating the ratio of each material's slope to the slope of CE2. Results of this experiment are summarized in the following table:

| Wear and Handling | | | |
|---|---|---|---|
| | Wear Ratio to CE2 | Standard deviation | Handling Assessment |
| EX1 | 0.34 | 0.06 | Good |
| EX2 | 0.36 | 0.01 | Good |
| EX3 | 0.36 | 0.08 | Good |
| EX4 | 0.45 | 0.13 | Good |
| EX5 | Not Tested | Not Tested | Good |
| CE1 | 0.24 | 0.05 | Poor |
| CE2 | 1.00 | 0.06 | Good |

What is claimed is:

1. A preformed semi-finished dental article comprising an uncured dental restoration composition comprising:
   a resin system comprising a free-radically polymerizable semi-crystalline resin having a molecular weight no greater than 3000 g/mole; and
   at least 50 wt-% of nanocluster filler wherein the nanocluster filler comprises primary particles having an average diameter of less than 100 nm;
wherein the uncured dental restoration composition has a first shape that is sufficiently malleable to be formed into a second shape.

2. A method of making a dental article comprising:
   providing a preformed semi-finished uncured dental article having a first shape wherein the uncured dental article comprises:
      a resin system comprising a free-radically polymerizable semi-crystalline resin having a molecular weight no greater than 3000 g/mole;
      at least 50 wt-% of nanocluster filler wherein the nanocluster filler comprises primary particles having an average diameter of less than 100 nm; and
      one more additional nanoscopic particulate filler present in an amount ranging from 15 wt-% to 30 wt-%;
   forming the semi-finished uncured dental article into a second shape; and
   hardening the semi-finished uncured dental article by curing.

3. A curable dental restoration composition comprising:
   a resin system comprising a free-radically polymerizable semi-crystalline resin having a molecular weight no greater than 3000 g/mole;
   at least 50 wt-% of nanocluster filler wherein the nanocluster filler comprises primary particles having an average diameter of less than 100 nm; and
   one more additional nanoscopic particulate filler present in an amount ranging from 15 wt-% to 30 wt-%.

4. The article of claim 1 wherein the semi-crystalline resin comprises polycaprolactone units.

5. The article of claim 1 wherein the semi-crystalline resin is a reaction product of a polycarprolactone diol and a hydroxyl reactive (meth)acrylate.

6. The article of claim 1 wherein the semi-crystalline resin is present in amount ranging from 1 wt-% to 15 wt-%.

7. The article of claim 1 wherein the resin system comprises at least one multi-(meth)acrylate aromatic monomer.

8. The article of claim 7 wherein the multi-(meth)acrylate aromatic monomer is a low shrinkage resin derived from bisphenol A.

9. The article of claim 8 wherein the low shrinkage resin is present in an amount ranging from 3 wt-% to 15 wt-% of the dental composition.

10. The article of claim 8 wherein the low shrinkage resin is present in an amount of at least 5 wt-% or 10 wt-%.

11. The article of claim 8 wherein the low shrinkage resin is BisGMA

12. The article of claim 8 wherein the resin system further comprises other polymerizable resins in addition to the low shrinkage resin in an amount of less than 20 wt-% of the total dental restoration composition.

13. The article of claim 12 wherein the other polymerizable resins are present in an amount no greater than 5 wt % of the dental composition.

14. The article of claim 1 wherein the composition further comprises one or more additional nanoscopic particulate fillers.

15. The article of claim 14 wherein the one or more additional nanoscopic particulate fillers are present in an amount ranging from 15 wt-% to 30 wt-%.

16. The article of claim 14 wherein the one or more additional nanoscopic particulate fillers comprise silica.

17. The article of claim 14 wherein the one or more additional nanoscopic particulate fillers comprise fumed silica.

18. The method of claim 2 wherein the semi-crystalline resin comprises polycaprolactone units.

19. The method of claim 2 wherein the semi-crystalline resin is a reaction product of a polycarprolactone diol and a hydroxyl reactive (meth)acrylate.

20. The method of claim 2 wherein the semi-crystalline resin is present in amount ranging from 1 wt-% to 15 wt-%.

21. The method of claim 2 wherein the resin system comprises at least one multi-(meth)acrylate aromatic monomer.

22. The method of claim 21 wherein the multi-(meth)acrylate aromatic monomer is a low shrinkage resin derived from bisphenol A.

23. The method of claim 22 wherein the low shrinkage resin is present in an amount ranging from 3 wt-% to 15 wt-% of the dental composition.

24. The method of claim 22 wherein the low shrinkage resin is present in an amount of at least 5 wt-% or 10 wt-%.

25. The method of claim 22 wherein the low shrinkage resin is BisGMA

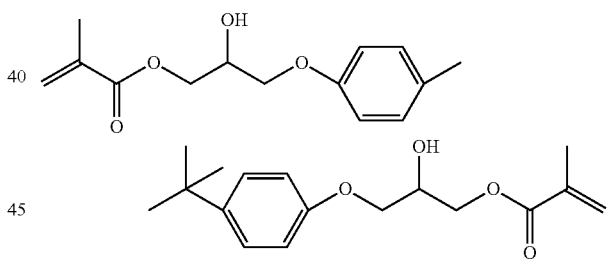

26. The method of claim 22 wherein the resin system further comprises other polymerizable resins in addition to the low shrinkage resin in an amount of less than 20 wt-% of the total dental restoration composition.

27. The method of claim 26 wherein the other polymerizable resins are present in an amount no greater than 5 wt-% of the dental composition.

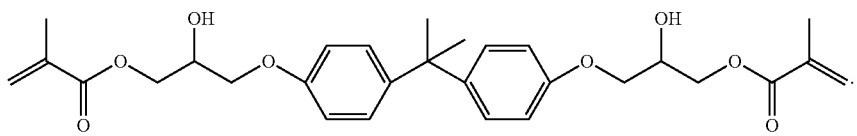

28. The method of claim 2 wherein the composition further comprises one or more additional nanoscopic particulate fillers.

29. The method of claim 28 wherein the one or more additional nanoscopic particulate fillers are present in an amount ranging from 15 wt-% to 30 wt-%.

30. The method of claim 28 wherein the one or more additional nanoscopic particulate fillers comprise silica.

31. The method of claim 28 wherein the one or more additional nanoscopic particulate fillers comprise fumed silica.

32. The curable dental restoration composition of claim 3 wherein the semi-crystalline resin comprises polycaprolactone units.

33. The curable dental restoration composition of claim 3 wherein the semi-crystalline resin is a reaction product of a polycarprolactone diol and a hydroxyl reactive (meth)acrylate.

34. The curable dental restoration composition of claim 3 wherein the semi-crystalline resin is present in amount ranging from 1 wt-% to 15 wt-%.

35. The curable dental restoration composition of claim 3 wherein the resin system comprises at least one multi- (meth) acrylate aromatic monomer.

36. The curable dental restoration composition of claim 35 wherein the multi-(meth)acrylate aromatic monomer is a low shrinkage resin derived from bisphenol A.

37. The curable dental restoration composition of claim 36 wherein the low shrinkage resin is present in an amount ranging from 3 wt-% to 15 wt-% of the dental composition.

38. The curable dental restoration composition of claim 36 wherein the low shrinkage resin is present in an amount of at least 5 wt-% or 10 wt-%.

39. The curable dental restoration composition of claim 36 wherein the low shrinkage resin is BisGMA

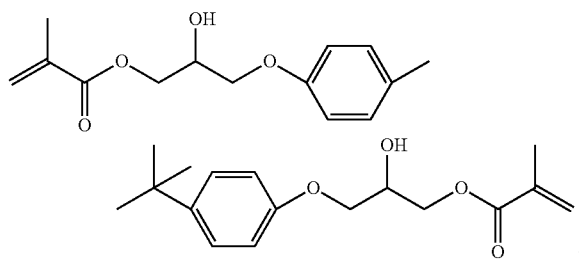

40. The curable dental restoration composition of claim 36 wherein the resin system further comprises other polymerizable resins in addition to the low shrinkage resin in an amount of less than 20 wt-% of the total dental restoration composition.

41. The curable dental restoration composition of claim 40 wherein the other polymerizable resins are present in an amount no greater than 5 wt-% of the dental composition.

42. The curable dental restoration composition of claim 3 wherein the composition further comprises one or more additional nanoscopic particulate fillers.

43. The method of claim 42 wherein the one or more additional nanoscopic particulate fillers are present in an amount ranging from 15 wt-% to 30 wt-%.

44. The method of claim 42 wherein the one or more additional nanoscopic particulate fillers comprise silica.

45. The method of claim 42 wherein the one or more additional nanoscopic particulate fillers comprise fumed silica.

* * * * *

UNITED STATES PATENT AND TRADEMARK OFFICE
CERTIFICATE OF CORRECTION

PATENT NO. : 8,906,981 B2  
APPLICATION NO. : 13/814974  
DATED : December 9, 2014  
INVENTOR(S) : Jie Yang Page 1 of 2

It is certified that error appears in the above-identified patent and that said Letters Patent is hereby corrected as shown below:

In the Specification

Column 5  
Line 23, delete "monomer" and insert -- monomer. --, therefor.

Line 47, delete "multi(meth)" and insert -- multi-(meth) --, therefor.

Line 48 (Approx.), delete "moities)" and insert -- moieties) --, therefor.

Line 49 (Approx.), delete "multi(meth)" and insert -- multi-(meth) --, therefor.

Column 6  
Line 8, delete "moities)" and insert -- moieties) --, therefor.

Line 16, delete "monomers" and insert -- monomers. --, therefor.

Line 49 (Approx.), delete "bisphenolA" and insert -- bisphenol A --, therefor.

Line 49 (Approx.), delete "ethoxylated bisphenolA" and insert -- ethoxylated bisphenol A --, therefor.

Column 8  
Lines 43-44, delete "polycarpolactone" and insert -- polycaprolactone --, therefor.

Column 9  
Line 26, delete "composition" and insert -- composition. --, therefor.

Column 10  
Line 42, delete "reference" and insert -- reference. --, therefor.

Signed and Sealed this  
Eighth Day of September, 2015

Michelle K. Lee  
*Director of the United States Patent and Trademark Office*

Column 16
Line 25 (Approx.), delete "Photoinitator" and insert -- Photoinitiator --, therefor.

Line 28 (Approx.), delete "Alpha" and insert -- Alfa --, therefor.

In the Claims

Column 21
Line 40, in Claim 5, delete "polycarpolactone" and insert -- polycaprolactone --, therefor.

Column 22
Line 6, in Claim 13, delete "wt %" and insert -- wt-% --, therefor.

Line 20, in Claim 19, delete "polycarpolactone" and insert -- polycaprolactone --, therefor.

Line 26, in Claim 22, delete "multi- (meth)" and insert -- multi-(meth) --, therefor.

Column 23
Line 18, in Claim 33, delete "polycarpolactone" and insert -- polycaprolactone --, therefor.

Line 24, in Claim 35, delete "multi- (meth)" and insert -- multi-(meth) --, therefor.

Column 24
Line 46, in claim 43 delete "method" and insert -- curable dental restoration composition --, therefor.

Line 49, in claim 44 delete "method" and insert -- curable dental restoration composition --, therefor.

Line 51, in claim 45 delete "method" and insert -- curable dental restoration composition --, therefor.